United States Patent
Scholly et al.

(10) Patent No.: US 8,197,398 B2
(45) Date of Patent: Jun. 12, 2012

(54) ENDOSCOPE

(75) Inventors: Werner Scholly, Denzlingen (DE); Stefan Schlenker, Freiburg (DE); Steffen Paul, Freiburg (DE); Volker Grimmig, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 992 days.

(21) Appl. No.: 12/170,651

(22) Filed: Jul. 10, 2008

(65) Prior Publication Data

US 2009/0018392 A1 Jan. 15, 2009

(30) Foreign Application Priority Data

Jul. 11, 2007 (DE) .................. 10 2007 032 202

(51) Int. Cl.
*A61B 1/04* (2006.01)
*A61B 1/06* (2006.01)

(52) U.S. Cl. ......................... 600/112; 600/160
(58) Field of Classification Search .................. 600/136, 600/125, 164, 132, 176
See application file for complete search history.

(56) References Cited

U.S. PATENT DOCUMENTS

| | | |
|---|---|---|
| 4,550,717 A | 11/1985 | Berger |
| 4,870,950 A | 10/1989 | Kanbara et al. |
| 4,905,082 A | 2/1990 | Nishigaki et al. |
| 5,498,230 A | 3/1996 | Adair |
| 5,682,199 A * | 10/1997 | Lankford ........................ 348/72 |
| 6,004,263 A * | 12/1999 | Nakaichi et al. ............. 600/176 |
| 6,106,457 A * | 8/2000 | Perkins et al. ................ 600/175 |
| 6,494,826 B1 | 12/2002 | Chatenever et al. |
| 6,676,598 B2 | 1/2004 | Rudischhauser et al. |
| 7,212,737 B2 | 5/2007 | Dehmel et |
| 2003/0088156 A1 | 5/2003 | Berci et al. |
| 2006/0281972 A1* | 12/2006 | Pease et al. ................... 600/109 |
| 2007/0078456 A1* | 4/2007 | Dumbauld et al. ............ 606/42 |
| 2007/0203554 A1* | 8/2007 | Kaplan et al. ................. 607/119 |

FOREIGN PATENT DOCUMENTS

| | | |
|---|---|---|
| DE | 19715510 | 10/1998 |
| DE | 19955180 | 12/2000 |
| DE | 102004009384 | 9/2005 |

* cited by examiner

*Primary Examiner* — Philip R Smith
*Assistant Examiner* — William Chou
(74) *Attorney, Agent, or Firm* — Volpe and Koenig, P.C.

(57) ABSTRACT

An endoscope (1) has a handle (2) as well as a probe part (3) that can be connected thereto via a coupling (4), with an illumination device as well as an eye-piece (17) with an imaging optic being arranged in the handle (2) and image conductors and light conductors in the probe part (3). The coupling includes an image interface and a light interface. In the coupling area, at least one axially engaging guide (6, 8) as well as bayonet-like engaging coupling parts (6, 5) are provided, one of which is embodied as a rotational locking part (5). In the final locked position the locking part (5) is secured by a snap. Preferably, the coupling (4) is provided with an axially engaging guide and additionally axially engaging guides (13, 15; 14, 16) are provided of the illumination system and the image transmission system, which are particularly arranged side-by-side.

10 Claims, 3 Drawing Sheets

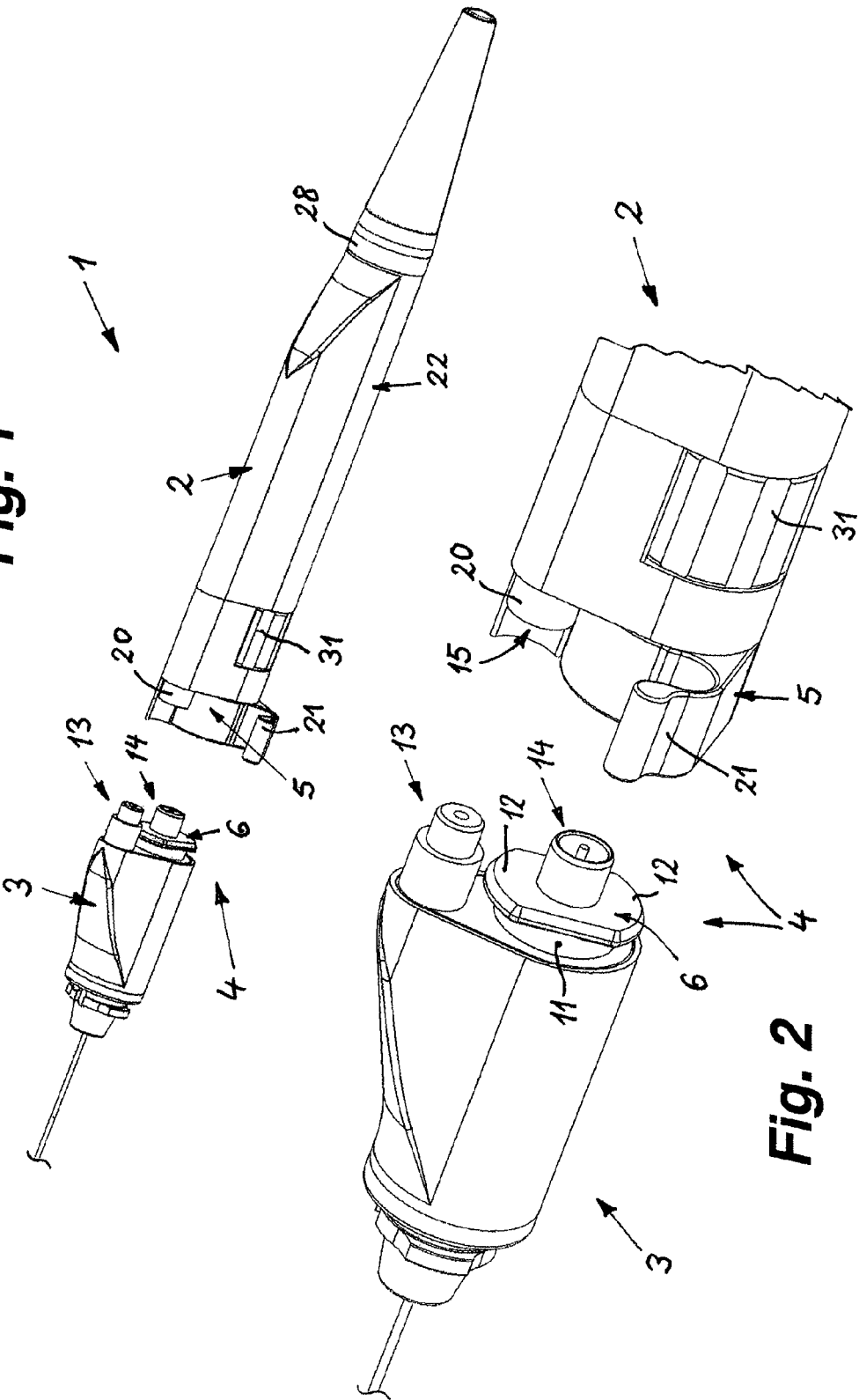

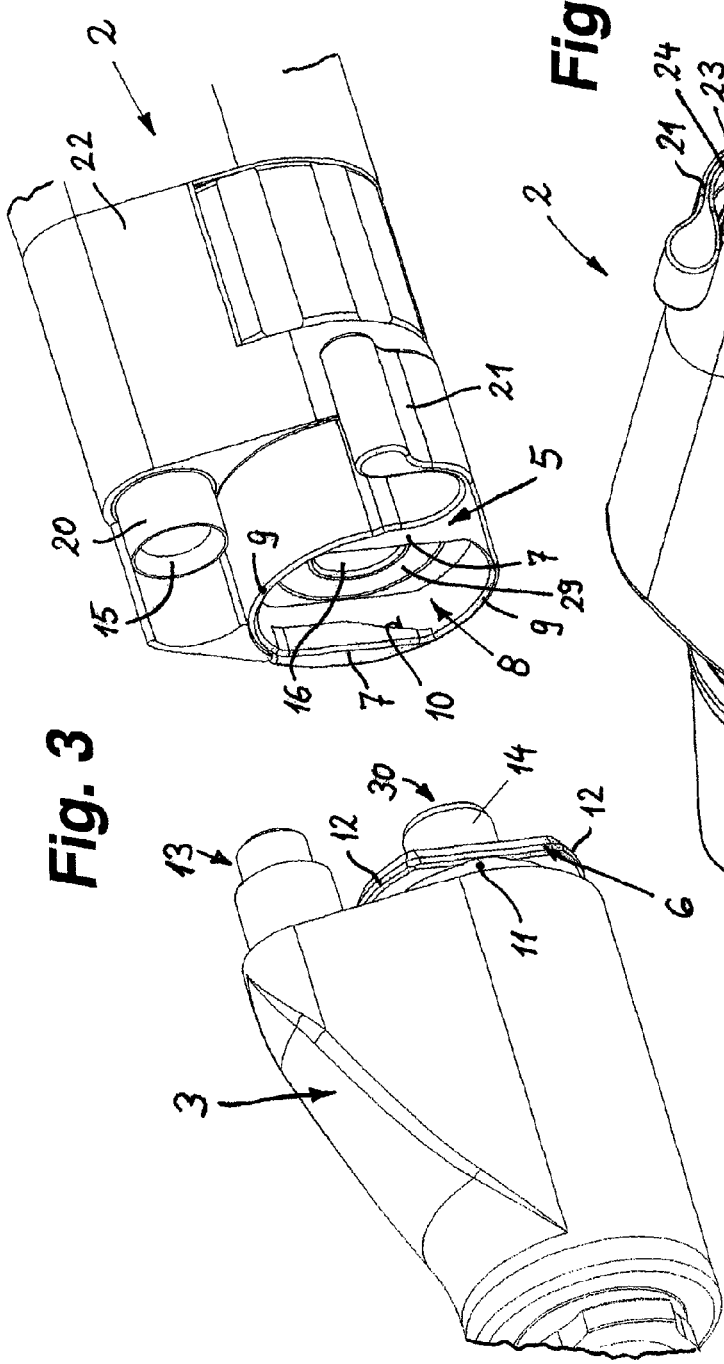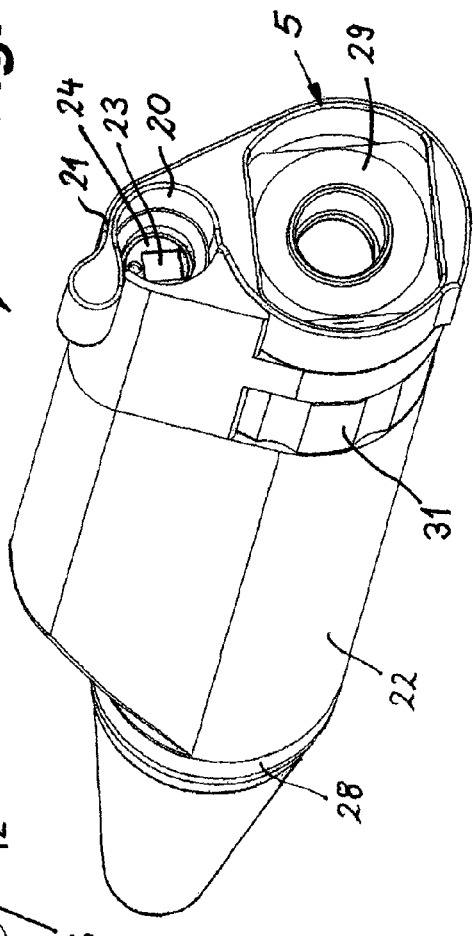

ENDOSCOPE

CROSS-REFERENCE TO RELATED APPLICATIONS

This application claims the benefit of DE 10 2007 032 202.1-51, filed Jul. 11, 2007, which is incorporated herein by reference as if fully set forth.

BACKGROUND

The invention relates to an endoscope with a handle as well as a probe part that can be connected thereto via a coupling, with an illuminating device as well as an eye-piece with an imaging optic being arranged in the handle and an imaging conductor and a light conductor in the probe part, and with the coupling being provided with an image interface and a light interface.

Endoscopes, with detachable handles for various interchangeable probes, are known from prior art in different embodiment variants with regard to the coupling. An essential requirement for such couplings comprises that they are simple and safely operated, unambiguous and, if applicable, can be operated without any visual control, and are protected from accidental opening. The known couplings fail to simultaneously fulfill all of the requirements.

SUMMARY

The object of the present invention is therefore to implement all these requirements combined in one coupling, thus to create a coupling which exhibits a simple design, high operational security, an unambiguous and simple operation, and which is also protected from accidentally opening.

In order to attain this object, at least one axially engaging guide is provided in the coupling area as well as coupling parts that engage each other in the form of bayonet fittings, one of which is embodied as a rotational locking part.

Here, the coupling itself can be provided with an axially engaging guide and additionally axially engaging guides of the illumination system can be provided, on the one hand, and of the image transmission system, on the other hand, which are arranged particularly side-by-side.

Mandatory guides are formed by the guides axially engaging each other, which allow the connection of the probe part and the handle only in a single position. Using the rotational locking part the two endoscope parts are pulled towards each other by the bayonet system and the plug-in connection is secured. This coupling requires only a few parts and can be simply locked and unlatched by rotating the locking part. Here, a snap can secure the locking part in its locked position to prevent an accidental opening.

For this purpose, the locking part can be provided with a flange-like appendage, on the one hand, as a handle for rotating the locking part and, on the other hand, for snapping.

In order to snap the locking part in the locked position the flange-like appendage of the locking part beneficially snaps over a protrusion, which preferably is formed by a sheath-shaped guiding part of the illumination part at the handle. Both the appendage of the locking part as well as the guiding part of the illumination system each fulfill therefore a dual function, so that parts can be omitted and the design is simplified.

Beneficially, the coupling with its coupling parts engaging each other is arranged coaxially in reference to the axially engaging guides of the eye-piece. Here, existing parts of the eye-piece and/or the eye-piece cartridge can simultaneously be used as fasteners for a coupling part, preferably the rotational locking part.

According to one embodiment, the locking part is embodied sheath-like with at least one interior locking protrusion and the other coupling part is embodied for an axial engagement in the locking part and for engaging behind the locking protrusion.

This way the coupling part introduced into the locking part can be engaged and fastened from behind by one or preferably several locking protrusions when the locking part is rotated.

The rotational locking part is preferably arranged at the handle and the coupling counterpart at the probe part. Particularly in interchangeable probes that are inserted only once or a few times, this is beneficial because the coupling counterpart is embodied simply and cost effectively as a plate-shaped part having a shape corresponding to the receiving openings of the locking part.

The illumination device located in the handle of the endoscope is beneficially provided with a light source mounted in the handle, particularly at least one light emitting diode, which is connected to the carrier element as a heat conducting body. This light emitting diode carrier element can here be thermally contacting the coupling between the handle and the probe part, with particularly a thermal connection to the locking part being provided.

The locking part therefore forms a cooling body by which the heat loss of the light source and perhaps of additional heat producing parts of the handle can be dissipated outward.

Heat radiation is particularly effective when the locking part is provided with a flange-like appendage serving as a handle, because in this way the surface for radiation is enlarged. Additionally, the light emitting diode carrier element can be connected to additional mounted parts of the handle, if applicable, and the probe part and/or housing parts for the purpose of heat dissipation.

Additional embodiments of the invention are disclosed in detail below.

BRIEF DESCRIPTION OF THE DRAWINGS

In the following the invention is explained in greater detail using the drawings. Shown are:

FIG. 1 is a perspective view of an endoscope with a handle and a probe part, shown separated from each other, FIG. 2 is an enlarged, perspective view of the probe part and a handle, separated from the probe part and shown partially, FIG. 3 is a view according to FIG. 2, however shown in a different perspective, FIG. 4 is a perspective view of a handle, looking to the end of the coupling in a closed locking part.

DETAILED DESCRIPTION OF THE PREFERRED EMBODIMENTS

Figures 5, 6:
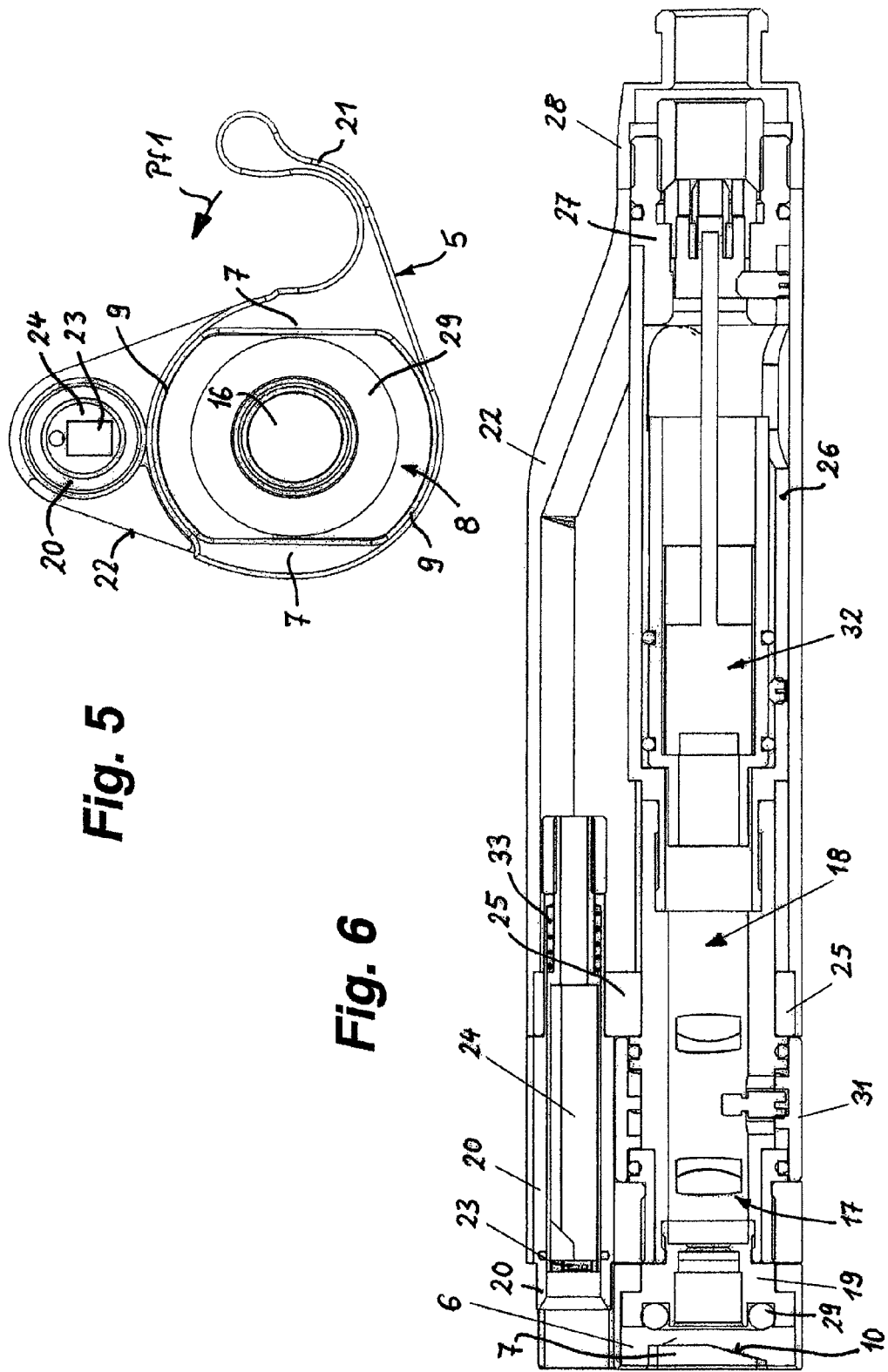
FIG. 5 is a side view of the face of the coupling end of the handle in an opened locking part.
FIG. 6 is a longitudinally cross-sectioned view of the handle.

An endoscope 1 is shown in FIG. 1 and essentially comprises a handle 2 as well as a probe part 3 that can be connected thereto. These two parts 2, 3 can be connected to each other via a coupling 4.

The coupling 4 comprises bayonet like coupling parts that engage each other, with a rotational locking part 5 being provided at the handle 2 and an essentially plate-shaped coupling counterpart 6 being provided at the probe part 3.

The rotational locking part 5 is embodied as a sheath with two diametrically opposite locking protrusion 7, protruding approximately radially inwardly (FIG. 3, 5). The other coupling part, forming the coupling counterpart 6, at the probe part 3 is formed to be engaged behind by the locking protrusions 7. In FIG. 5 it is well discernible that the rotational locking part 5 comprises a receiving opening 8 for the coupling counterpart 6, which on the one hand is limited by opposite arranged circular arc sections 9 and, on the other hand, by segmental locking protrusions 7 located between these circular arc sections in the circumferential direction.

In FIG. 3 it is discernible that the locking protrusions 7 have inclines 10, arranged axially inside, which in the locked position engage behind the plate-shaped coupling counterpart 6 and clamp it tightly. The plate-shaped coupling counterpart 6 has a shape corresponding to the form of the receiving opening 8 and is connected fixed to the probe part 3.

In FIGS. 2 and 3, it is discernible that the coupling counterpart 6 comprises distally a spacer 11, embodied such that the segmental sections 12 engaging behind the locking protrusions 7 remain clear at their back side. By the design of the plate-shaped coupling counterpart 6 with two opposite segment sections 12 and the two flat sides, located therebetween and facing each other, the coupling counterpart 6 fits precisely pre-centered into the receiving opening 8, such that the insertion during coupling of the probe part 3 to the handle 2 can only occur in a single position.

The axially engaging guides of the illumination system, on the one hand, and those of the image transmission system, on the other hand, contribute to this purpose. Here, pins 13, 14 are provided at the probe part 3 and openings 15, 16 are provided at the handle 2 in sheath-like parts, in which the respective pins engage. The coupling 4 with its engaging coupling parts in the form of the rotational locking part 5 and the coupling counterpart 6 is arranged coaxially in reference to the axially engaging guides formed by the respective pin 14 and opening 16 of the eye-piece 17.

An eye-piece cartridge 18 is provided in the handle, which comprises a holding plate 19 at its end facing the coupling (FIG. 6). The rotational locking part 5 of the coupling 4 is located at this holding plate 19 and arranged coaxially in reference to the eye-piece cartridge 18. In FIGS. 1 through 3 and 5, the locking part 5 is arranged in the open position and can be pivoted according to the arrow Pf 1 in FIG. 5 by approximately 90° into the locked position. The locked position is discernible in FIG. 4. In this locked end position the rotational locking part 5 is secured by a snap. For this purpose, a sheath-like guiding part 20 of the illumination system at the handle 2 is used for snapping over. The rotational locking part 5 is provided with a flange-like appendage 21, which also serves as a snapping element and snaps over the guiding part 20 in the locked position.

Furthermore, this appendage serves as a handle for rotating the locking part 5. As clearly discernible in FIG. 4, the flange-like appendage is located, except for its far end, largely inside the perimeter of the handle housing 22 in the locked position, thus is not protruding in a disturbing manner.

A light source is provided within the handle, as a part of the illumination device, in the present case a light diode 23, which is connected to a carrier element 24 as a heat conducting body. This carrier element 24 is thermally connected to the coupling 4 for dissipating the heat loss of the light emitting diode 23. The thermal connection is here formed, on the one hand, between the carrier element 24 via the tubular guide part 20 to the appendage 21 of the locking part 5 and on the other hand the carrier element 24 is connected to the eye-piece cartridge 18 via a holder 25, which cartridge in turn is thermally connected via the holding plate 19 to the locking part 5 of the coupling 4. This way, the heat of the light source developing is guided outward and there dissipated to the environmental air. In the coupled position, the coupling counterpart 6 of the probe part 3 contributes to the heat dissipation via the locking part 5.

In the coupled position, the off-set fiber-optic pin 13 of the probe part 3 engages the tubular guiding part 20 of the handle 2 with its free stop, smaller in diameter, and the circular facial surface of the guide part 20 contacts the stop of the pin 13, larger in its diameter. This separating part is positioned such that in the locked position of the locking part 5, it is snapped over by its flange-like appendage 21 and bridged. The appendage 21 therefore forms another heat bridge, by which the heat is transferred and dissipated from the guiding part 20 to the pin 13 and thus to the probe part 3.

In this way, the coupling parts also serve as external cooling bodies for the light source located in the handle and, if applicable, for additional parts located in the housing of the handle creating heat loss.

Finally, heat transfer to the cap nut 28 abutting at the rear occurs via the eye-piece cartridge 18 as well as a camera socket 26 and a holding socket 27 located at the rear end of the housing 22, such that even at this rear end heat transfer occurs towards the outside.

At the holding plate 19 for the eye-piece 18, a gasket 29 is located within a circular groove, which the plate-shaped coupling counter-piece 6 contacts in the locked position of the coupling and thus seals the overall system in a watertight manner.

The carrier element 24, which is rod-shaped, for the light diode 23 is supported mobile in the longitudinal direction and supported by a spring 33 at the back. When coupling the probe part 3, the off-set fiber-optic pin 13 presses against the LED 23, with the mobile illumination unit with the LED 23 and the carrier element 24 deflects into the tubular guide part 20 against the spring force. In the coupled position, the illumination unit is constantly pressed against the fiber-optic pin 13 by the spring pressure such that an optimal light transmission is given. Additionally, heat is also guided off to the probe part 3 via this contact point.

Finally, the elastic support of the carrier element 24 ensures that the light transmission end surfaces of the eye-piece, on the one hand, and the image conducting bundle located in the pin 14 of the probe part 3, on the other hand, are precisely allocated in reference to each other, particularly are supported on each other.

When coupling an interchangeable probe to a handle 2, the probe with its coupling counterpart 6 is inserted into the open locking part 5. Using the pin 13 and the opening 15 in the guide part 20, a second mandatory guide is formed which is arranged eccentrically. Therefore, the insertion can occur in one position only, and thus application errors are avoided. The optic acceptance surface 30 of the probe part 3 is also pre-centered in the handle by this insertion. By rotating the locking part 5, the two inclines 10 of the locking protrusions 7 abut at the rear on the segment sections 12 of the coupling counterpart 6, and thus engage behind them such that the probe part 3 is pulled towards the handle 2. Here, the plate-shaped coupling counterpart 6 is pressed onto the gasket 29 and thus a sealed system is ensured. In the final locked position the appendage 21 snaps into the fiber-optic pin formed by the guide part 20 such that the locking part 5 is ensured from accidental opening.

At the handle 2, focusing is provided with the focusing ring 31, by which focusing on the optic image recognition surface 30 can occur after the probe part 3 has been coupled, and thus an optimally focused image is created on the CCD of the camera 32 located in the camera socket 26.

Through the use of the coupling 4 according to the invention, very compact and also miniaturized endoscopes can be realized. Simultaneously, a cost-effective and simple design of the coupling is achieved. Here, the coupling essentially comprises only two parts.

The invention claimed is:

1. An endoscope comprising a handle and a probe part that can be connected thereto via a coupling, with an illumination device as well as an eye-piece with an imaging optic being arranged in the handle and image conductors and light conductors being arranged in the probe part, the coupling comprising an image interface and a light interface between the handle and the probe part including at least one axially engaging guide as well as bayonet-type engaging coupling parts provided in a coupling area, one of which comprises a rotational locking part, wherein, in a locked position, the rotational locking part is secured by a snap, wherein the rotational locking part is arranged at the handle and an other of the bayonet-type engaging coupling parts comprises a coupling counterpart that is arranged at the probe part, the rotational locking part is provided with a flange-like appendage as a handle for rotating the rotational locking part, and the flange-like appendage of the rotational locking part is located in a locked position at least largely within a perimeter contour of the housing of the handle, wherein for snapping the rotational locking part into the locked position, the flange-like appendage of the rotational locking part snaps over a protrusion in the locked position, which is formed by a sheath-shaped guide part of the illumination system at the handle and a pin located at the probe part.

2. An endoscope according to claim 1, wherein the coupling comprises an axially engaging guide and additional axially engaging guides of the illumination system and the image transmission system, which are arranged side-by-side.

3. An endoscope according to claim 2, wherein the coupling with the engaging coupling parts is arranged coaxially in reference to the axially engaging guides which are located on an eye-piece.

4. An endoscope according to claim 1, wherein the rotational locking part has a sheath-like form with at least one interior locking protrusion and the other coupling part of the bayonet-type engaging coupling parts is embodied for an axial engagement in the rotational locking part and for being engaged to by the at least one locking protrusion.

5. An endoscope according to claim 4, wherein the rotational locking part forms the at least one axially engaging guide and includes a receiving opening deviating from a round shape, the other coupling part that comprises the coupling counterpart has a shape approximately equivalent to the shape of the receiving opening that is adapted to enter the receiving opening and for being engaged to the at least one locking protrusion.

6. An endoscope according to claim 4, wherein in an area of a receiving opening of the rotational locking part, the rotational locking part is provided with an approximately round shape and includes two of the locking protrusions that point inwardly and are positioned diametrically opposite one another and are segment-shaped, with inclines being arranged inside for impingement of the coupling counterpart.

7. An endoscope according to claim 1, wherein the coupling comprises an axially engaging guide and additional axially engaging guides of the illumination system and the image transmission system, which are arranged side-by-side and the guides of the illumination system and the image transfer system that engage each other in the area of the coupling are provided with openings at the handle and with the pin and an additional pin that engage the openings at the probe part.

8. An endoscope according to claim 1, wherein the illumination device comprises a light source located in the handle, which is connected to a carrier element as a heat conducting body, and the carrier element is in a thermal contact at least to the coupling between the handle and the probe part, including the rotational locking part and the flange-like appendage connected thereto, as well as additional parts of the handle and the probe part and/or the housing parts.

9. An endoscope according to claim 8, wherein in the locked position of the locking part, the flange-like appendage bridges and thermally couples engaging parts of the handle and the probe part, including the tubular guide part of the handle for supporting the carrier element and the fiber-optic pin of the probe part.

10. An endoscope comprising a handle and a probe part that can be connected thereto via a coupling, with an illumination device as well as an eve-piece with an imaging optic being arranged in the handle and image conductors and light conductors being arranged in the probe part, the coupling comprising an image interface and a light interface between the handle and the probe part including at least one axially engaging guide as well as bayonet-type engaging coupling parts provided in a coupling area, one of which comprises rotational locking part, and wherein, in a locked position, the rotational locking part is secured by a snap, wherein the illumination device comprises a light source located in the handle, which is connected to a carrier element as a heat conducting body, and the carrier element is in a thermal contact at least to the coupling between the handle and the probe part, including the rotational locking part and a flange-like appendage connected thereto, as well as additional parts of the handle and the probe part and/or the housing parts, wherein in the locked position of the locking part, the flange-like appendage bridges and thermally couples engaging parts of the handle and the probe part, including a tubular guide part of the handle for supporting the carrier element and a fiber-optic pin of the probe part, and wherein the carrier element is supported for movement in a longitudinal direction and is contacted at one end thereof by a spring.

* * * * *